United States Patent [19]

Fang

[11] 4,116,890

[45] Sep. 26, 1978

[54] PHOSPHONATED FLUOROTELOMERS

[75] Inventor: James Chen-Shang Fang, Media, Pa.

[73] Assignee: E. I. Du Pont De Nemours and Company, Wilmington, Del.

[21] Appl. No.: 764,174

[22] Filed: Feb. 2, 1977

Related U.S. Application Data

[63] Continuation-in-part of Ser. No. 663,071, Mar. 2, 1976, abandoned.

[51] Int. Cl.$^2$ ............................................. C25B 13/00
[52] U.S. Cl. .................................... 521/28; 204/296; 260/927 R; 260/932; 521/27; 521/38
[58] Field of Search ................. 204/252, 98, 258, 295, 204/296; 260/29.6 F, 42.27, 2.2 R, 95, 927 R; 526/247, 249, 254, 253

[56] References Cited

U.S. PATENT DOCUMENTS

| | | | |
|---|---|---|---|
| 2,786,827 | 3/1957 | Barnhart | 526/249 |
| 3,054,785 | 9/1962 | Wade | 526/449 |
| 3,515,776 | 6/1970 | Baranoeukos et al. | 260/932 |
| 3,538,196 | 11/1970 | Baranoeukos et al. | 260/932 |
| 3,645,991 | 2/1972 | Mersosian | 526/247 |
| 3,853,720 | 12/1974 | Korach et al. | 204/295 |
| 3,853,721 | 12/1974 | Darlington et al. | 204/296 |
| 3,980,613 | 9/1976 | Barlnot et al. | 260/29.6 F |

*Primary Examiner*—Joseph L. Schofer
*Assistant Examiner*—Peter F. Kulkoshy

[57] ABSTRACT

The phosphonated fluorotelomers of this invention are, or can easily be made to be, hydrophilic. When blended with inert fibrous materials they can be used to make diaphragms for electrolytic cells, particularly for chlor-alkali cells used in the production of chlorine, hydrogen and sodium hydroxide from brine. Ion-exchange membranes can also be made from these fluorotelomers. The fluorotelomers can be made by using free radical phosphonyl esters to terminate the polymerization of the selected fluorocarbons.

22 Claims, No Drawings

PHOSPHONATED FLUOROTELOMERS

CROSS REFERENCES TO RELATED APPLICATION

This application is a continuation-in-part of copending application Ser. No. 663,071, filed Mar. 2, 1976, now abandoned and assigned to the assignee of the present application.

BACKGROUND OF THE INVENTION

In commercial chlor-alkali cells used for the production of chlorine, hydrogen and sodium hydroxide from brine, asbestos diaphragms are ordinarily used to separate the anolyte and catholyte compartments. Diaphragms of this sort are generally satisfactory, but their electrical resistance is high and cells which use such diaphragms therefore require more electric current for operation than is desirable. Furthermore, asbestos diaphragms treated with certain ion-exchange resins are described in U.S. Pat. No. 3,853,721 — Darlington and Foster (1974), incorporated herein by reference.

SUMMARY OF THE INVENTION

The phosphonated fluorotelomers of the invention are those represented by the formula

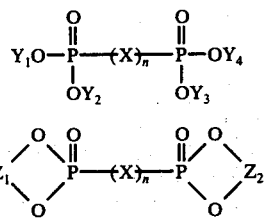

where $Y_1$, $Y_2$, $Y_3$ and $Y_4$ are the same or different and are alkyl radicals of 1-10 carbon atoms, alkyl radicals of 1-10 carbon atoms substituted with at least one alkyl radical of 1-4 carbon atoms, or monovalent metals;

X is a homo- or cotelomeric moiety of at least one of
(a) one or more monoethylenically unsaturated monomers fully substituted with fluorine atoms or with a combination of at least one fluorine atom and chlorine or bromine atoms, and
(b) a perfluoroalkyl vinyl ether whose alkyl group contains 1-10 carbon atoms;

$Z_1$, and $Z_2$ are the same or different and are divalent metals, alkylene radicals of 1-10 carbon atoms, or alkylene radicals of 1-10 carbon atoms substituted with at least one alkyl radical of 1-4 carbon atoms, or $Z_2$ is made up of $Y_1$ and $Y_2$; and $n$ is 2-500.

As used in formulas (1) and (2), "cotelomeric moiety" means a telomeric moiety composed of two or more different types of monomer units, and "homotelomeric moiety" means a telomeric moiety composed of one type of monomer units.

The term "fully substituted" means that few if any C-H bonds are found in the telomeric moiety. Although preferred, the telomer need not be completely substituted.

The telomers of formula (1) can also be in the form of trivalent metal salts, which have a cross-linked structure in which one or two of the metal valences are taken by one fluorotelomer molecule and the remaining valences are taken by other fluorotelomer molecules. The monovalent, divalent and trivalent metal salts of the fluorotelomers can be formed in situ in a chloralkali cell where the fluorotelomer is used.

Those fluorotelomers of formulas (1) and (2) which are not hydrophilic or are only marginally hydrophilic can be made hydrophilic by converting them to the free acid forms or to metal salts, as will be described.

The phosphonated fluorotelomers preferred for use according to the invention because they are easy to prepare and because they have good ion-exchange characteristics and low solubility in cell liquors are those of formula (1) where X is a telomeric moiety of tetrafluoroethylene (TFE);
$Y_1$, $Y_2$, $Y_3$, and $Y_4$ are all ethyl or all butyl, or where $Y_1$ and $Y_2$ are ethyl and $Y_3$ and $Y_4$ are butyl; and
$n$ is 20-100.

Also preferred for their low melting points and the ease with which diaphragms can be fabricated with them are fluorotelomers of formula (1) where X is cotelomeric moiety of TFE and a perfluoropropyl vinyl ether in a weight ratio of 83/17, or a telomeric moiety of hexafluoropropylene; $Y_1$, $Y_2$, $Y_3$ and $Y_4$ are all ethyl; and
$n$ is 20-100.

Also prreferred in some circumstances are fluorotelomers of formula (2) where

X is cotelomeric moiety of TFE and hexafluoropropylene (HFP) in a weight ratio of 5/1;
$Z_1$ is ethylene and $Z_2$ is diethyl; and
$n$ is 20-100.

Parts, percentages and proportions herein are by weight except where indicated otherwise. In actual use, the preferred telomers are converted to the corresponding sodium salts in an electrolytic cell.

In addition to the fluorotelomers themselves, the invention also comprises processes for their preparation in the ester, acid and salt forms, diaphragms and membranes made using them, and the use of such diaphragms and membranes.

DETAILED DESCRIPTION OF THE INVENTION

Unlike ordinary fluorotelomers, the fluorotelomers of this invention are hydrophilic or can easily be made to be hydrophilic. "Hydrophilic" in this sense means the telomers absorb water rather than repel it. More specifically, "hydrophilic" means that the telomer has a water contact angle of 0° to about 50°, as measured by the method and apparatus described on page 137 of "Contact Angle, Wettability and Adhesion," American Chemical Society, 1964.

The claimed hydrophilic fluorotelomers, when blended with inert fibrous materials and binders and fabricated into diaphragms, or when formed into a membrane preferably supported by an inert fabric, can be used in ion-exhcnage procedures, especially where hydrophilicity is desirable or essential. Such diaphragms used in chloralkali cells, surprisingly have far less electrical resistance than conventional asbestos diaphragms. As a result, cells using diaphragms containing the hydrophilic fluorotelomers of the invention can maintain chlorine, hydrogen and caustic production at the same levels obtained when asbestos diaphragms are used even though the cells operate at lower voltages. In addition, diaphragms made with these fluorotelomers in general are more resistant to attack by electrolytic cell liquors, last longer and are more dimensionally stable than prior art asbestos diaphragms.

How the Phosphonated Fluorotelomers are Made

The phosphonated fluorotelomers of the invention can be made by reacting a suitable monoethylenically unsaturated fluoromonomer with a compound capable of generating a phosphorous-containing free radical of the structure

where $Y_1$ and $Y_2$ are the same or different and preferably are alkyl radicals of 1-10 carbon atoms.

Illustrative of the fluoromonomers which can be used are tetrafluoroethylene (TFE)
monochlorotrifluoroethylene
dichlorodifluoroethylene
monobromotrifluoroethylene
dibromodifluoroethylene
hexafluoropropylene (HFP)
perfluoroalkyl vinyl ethers (whose alkyl groups contain 1-10 carbon atoms)

These fluoromonomers can be used singly to produce homotelomeric forms, or can be used in combinations of two or more to form cotelomeric forms of the phosphonated fluorotelomers.

Illustrative of the compounds capable of generating the requisite phosphorous-containing free radical are tetraalkyl hyphosphates (whose alkyl groups contain 1-10 carbon atoms)
tetraalkyl pyrophosphites (whose alkyl groups contain 1-10 carbon atoms)
cycloalkyl hypophosphates (whose alkyl groups contain 1-10 carbon atoms)
cycloalkyl pyrophosphites (whose alkyl groups contain 1-10 carbon atoms) and
compounds of the formula

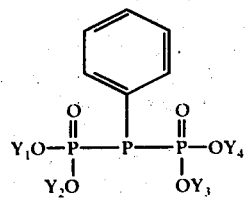

where $Y_1$, $Y_2$, $Y_3$ and $Y_4$ are defined as in formula (1). Mixtures of such compounds can also be used.

The reaction of the fluoromonomer and free radical generating compound proceeds according to the following illustrative equations:

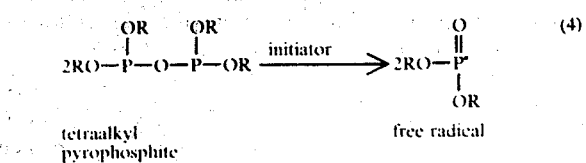

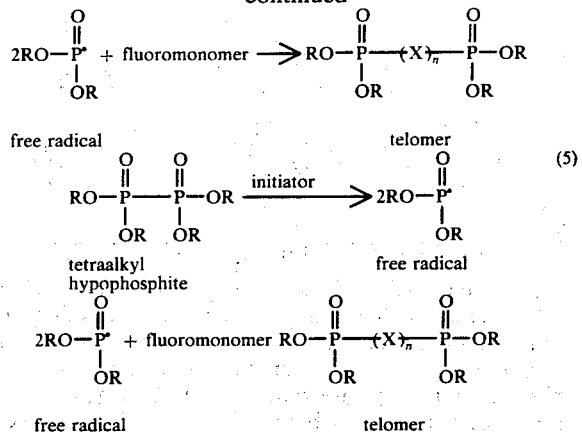

The same reactions can be used to prepare the telomers of formula (2), using cycloalkyl hypophosphates or cycloalkyl pyrophospites as free radical generating compounds.

The reactions described in equations (4) and (5) are carried out by first dissolving enough of the hypophosphate or pyrophosphite reactant in a halogenated hydrocarbon solvent to make a 1—50% by weight solution. To this solution is then added 0.1-10%, by weight, of a free radical initiator like di-t.butyl peroxide or azobisisobutyronitrile.

The solution is then placed in a pressure vessel and the fluoromonomer gas or liquid is added. The amount of fluoromonomer added will depend on the telomer chain length desired [i.e. the value of n in formulas (1) and (2)] and ordinarily is in the range of 2-500 moles for each two moles of pyrophosphite or hypophosphate.

The vessel is then sealed, heated to 50°-300° C, preferably 60°-120° C and held there, with rocking, until the pressure in the vessel drops, which indicates completion of the reaction. The vessel is then opened, the dispersion of phosphonated fluorotelomer removed and the solvent stripped from the dispersion by evaporation. The resulting product is washed in methanol, dried and is then ready for use.

The fluorotelomer thus isolated can vary in physical state from a viscous liquid to a waxy solid.

The mixed telomers of the invention, i.e., those in which $Y_1$ and $Y_2$ are different from $Y_3$ and $Y_4$, can be prepared according to the following illustrative equations:

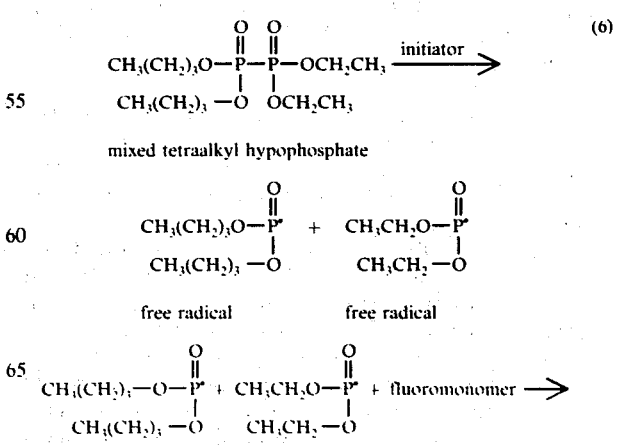

-continued $$CH_3(CH_2)_3-O-\underset{\underset{CH_3(CH_2)_3-O}{|}}{\overset{\overset{O}{\|}}{P}}-(X)_n-\underset{\underset{O-CH_2CH_3}{|}}{\overset{\overset{O}{\|}}{P}}-O-CH_2CH_3$$

telomer

The reaction described in equation (6) is carried out in the same way as those of equations (4) and (5).

In the formation of the free radicals, some different terminal groups, such as carboxyl groups, may be introduced. However, this would not affect the ability of the described fluorotelomers which are still present to provide the advantages of the invention.

The mixed tetraalkyl hypophosphate reactant used in equation (6) can be prepared as described in Bull. Acad. Polon. Sci., Ser. Sci. Chim., 13, 253 (1965) and in Z. Anorg. Allg. Chem., 288, 171 (1956).

The metal salts of the phosphonated fluorotelomers can be prepared by hydrolyzing a telomer to the free acid form, then replacing the hydrogens of the carboxyl groups with metals by metathesis.

Monovalent, divalent or trivalent metals can be used to form a fluorotelomer salt. Illustrative of such metals are
  sodium
  potassium
  lithium
  calcium
  barium
  magnesium
  aluminum
  manganese
  iron
  cobalt
  copper
  zinc
  cadmium Ordinarily, the fluorotelomers are used in the ester form to make diaphragms for chloralkali cells. The ester form is converted to the sodium salt form when the diaphragm comes into contact with sodium hydroxide in the cel liquor. The ester form is also readily converted to the acid form by hydrolysis such as with suitable acids.

How Diaphragms of the Telomers are Made

For whatever use, a diaphragm using a phosphonated fluorotelomer of the invention can be prepared from a composition which comprises
  (a) one or more fluorotelomers of formula (1);
  (b) a fibrous material which will act as a base for the diaphragm;
  (c) a fluoropolymer binder material; and
  (d) a liquid carrier.

This composition can also contain conventional adjuncts such as wetting agents, surfactants, defoamers and the like, in the usual amounts.

A diaphragm can be made from such a composition by first deagglomerating the fibers of (b) and then forming a mat of the fibers by removing the carrier, preferably by a papermaking technique. The mat is then heated to the binder fusion temperature, to give a coherent structure which can be used directly for whatever purpose intended.

The diaphragm mat can be formed directly on the cathode screen of the electrolytic cell in which it is to be used and then heated to fuse the binder. The diaphragm thus made can be used directly, without further treatment. Diaphragms made in this way must meet manufacturer's specifications regarding permeability, current efficiency and dimensional stability. These specifications vary with the manufacturer, the type of cell being used, electrical current demands of the cell, and like factors. One skilled in the diaphragm making art will use the same skills in preparing diaphragms from the compositions of this invention that he does in preparing conventional asbestos diaphragms.

Any fibrous material can be used which can withstand the baking temperature to be used and which resists attack by the environment in which the membrane is to be used. Illustrative of such materials are
  asbestos
  glass fibers
  fibers of such fluoropolymers as polytetrafluoroethylene (PTFE) or TFE/HFP copolymers
  potassium titanate fibers.

Mixtures of such fibrous materials can also be used. Asbestos is the preferred fibrous material for use in electrolytic cell diaphragms. Especially preferrred is a chrysotile asbestos whose fibers have an average diameter of about 200A° (as measured by electron microscopy) and an average length of about 70 mm. Preferably, the asbestos fibers are completely or substantially completely coated with fluorotelomers of the invention.

Similarly, the fluoropolymer to be used as a binder material can be any which resists attack by the environment in which it is to be used. Illustrative are
  PTFE
  TFE/HFP copolymers (all monomer ratios).
  polyvinyl fluoride
  polyvinylidene fluoride
  vinylidene fluoride/HFP copolymers (all monomer ratios).

Mixtures of binder materials can also be used. Mixtures of binder materials can also be used.

In electrolytic cell diaphragms, the TFE/HFP copolymers are preferred as binder materials because of their inert nature.

The carrier can be any liquid which will not significantly affect the chemical or physical characteristics of the diaphragm. Illustrative of such liquids are
  water
  chlorinated hydrocarbons
  methanol
  hexane
  brine.

When the composition is to be used to make an electrolytic cell diaphragm, brine solution of 15% NaCl in water is preferred as a carrier because it helps keep the fibrous material in suspension.

The components of the composition are preferably present in the following concentrations:
  (a) Telomer — 10–90% by weight of the total of (a) and (b), even more preferably 40–60%,
  (b) Binder — 10–90% by weight of the total of (a) and (b), even more preferably 40–60%;
  (a) plus (b) constituting 10–90%, preferably 20–25%, by weight of the total of (a), (b), and (c);
  (c) Fibrous material — 10–90% by weight of the total of (a), (b), (c), preferably 70–80%;
  (d) Carrier — the remainder.

The composition will contain 0.01–3%, by weight, of solids, preferably about 1%.

In a variant of this composition, an appropriate amount of the telomer and binder can be mixed together, and the fibrous material and carrier can be added to this mixture just before the resulting composition is to be used to prepare a diaphragm.

In such a composition, the telomer and binder are each present in concentrations of 1–99%, preferably 10–90%, by weight of the total of telomer and binder.

Although it is expected that the phosphonated fluorotelomers of the invention will be used primarily to fabricate diaphragms for electrolytic cells, especially chloralkali cells, they can also be used to prepare membranes for use as the separating means for separating diverse substances, either electrolytically or nonelectrolytically. For instance, they may be used in ion-exchange procedures such as the desalinization of sea water, and to prepare semipermeable membranes for use in osmotic procedures and in dialysis, including Donnan dialysis. The telomers can also be used to prepare battery separators, especially for use in alkaline cells. Fluorotelomers of formulas (1) and (2) where $n$ is 2–20 can also be used to passivate metals.

Membranes differ from diaphragms in that membranes are substantially hydrolytically impermeable, selectively passing either cations or anions, depending on the permselectivity of the membrane. Semipermeable membranes also have minute porosity permitting the passage of liquids but inhibiting the passage of relatively large species such as some colloids. Diaphragms do pass substantial amounts of fluid while inhibiting the passage of anions or cations.

Membranes may be formed and used according to techniques known in the art. Phosphonated fluorotelomers of the invention may be formed into membranes, preferably about 0.1–0.25 mm thick in contrast to typical diaphragm thicknesses of 2.5 mm. Such thin membranes would normally be formed on a fabric, preferably of open mesh design, of material which is inert to the operating environment. Fluorocarbon polymers such as PTFE are suitable to support phosphonated fluorotelomers of the invention to be used in chlor-alkali cells.

The following examples illustrate the invention. In each example, the diaphragms prepared were used with a cathode-to-anode spacing of 0.735 cm (¼ in.). Typical asbestos diaphragm cells of the prior art require 3.5–3.7 volts to obtain a current density of 0.204 amperes per square centimeter with that spacing. Although the diaphragms of the examples are formed as sheets and then placed into electrolytic cells, similar results are obtained when the diaphragms are formed on a cathode screen in the cell.

EXAMPLE ONE (A) A pressure vessel was charged with

| | | | |
|---|---|---|---|
| (1) | trichlorotrifluoroethane | 160 | parts |
| (2) | a solution of 6.45 parts of tetraethyl pyrophosphite in 20 parts of trichlorotrifluoroethane | | |
| (3) | a solution of 2 parts of ditertiary butyl peroxide in 20 parts of trichlorotrifluoroethane | | |
| (4) | tetrafluoroethylene | 50 | parts |

The charge was blanketed with nitrogen, the vessel sealed and the temperature of the charge raised to 100° C and held there for 2 hours. The temperature of the charge was then raised to 120° C, held there for 2 hours, then raised still again to 140° C and held at that temperature for 2 hours. At that point, a drop in pressure inside the vessel indicated completion of the reaction.

The vessel was opened, the contents removed and placed in a still, where the solvent was distilled off at 40°–50° C.

The resulting waxy solid was washed twice with methanol and then dried under vacuum.

(B) The following were prepared:
(1) a solution of 363 parts of sodium chloride in 2420 parts of distilled water.
(2) a mixture of
 (a) 5.5 parts of a TFE/HFP 85/15 copolymer dispersion, 55% solids in water, and
 (b) 3.03 parts of the product of (A) in 30 parts of isopropanol.

Solution (1) was placed in a blender, to which was then added 24.2 parts of asbestos fibers (average diameter 200Å, average length 70 mm, sold by Johns-Manville Co. as Chlorbestos SP-25.) Mixture (2) was then added. The charge was blended at medium speed for 2 minutes and then sparged with air for two hours to deagglomerate the asbestos fibers.

This mixture was then diluted with an equal volume of distilled water and poured into a sheet mold, where the liquid was drawn off under a vacuum of 250 mm. The resulting mat was washed by drawing 2000 parts of distilled water through it and was then dried at 95° C for 1 hour and then baked at 275° C for 30 minutes, to give a product 2.5 mm thick.

The mat was then boiled in 5% aqueous sodium hydroxide for 2.75 hours and dried.

(C) The mat prepared in (B) was put in the diaphragm position on the cathode of a chlor-alkali cell, where, in operation, it required an average voltage of 3.7 to achieve a current density of 0.204 amperes per square centimeter of diaphragm area.

EXAMPLE TWO (A) A fluorotelomer was prepared as described in Example 1 (A) using the following charge

| | | | |
|---|---|---|---|
| (1) | a solution of 16.5 parts of dibutyl-diethyl hypophosphate in 200 parts of trichlorotrifluoroethane | | |
| (2) | azobisisobutyronitrile | 4.1 | parts |
| (3) | tetrafluoroethylene | 50 | parts | and holding the reaction temperature at 65° C for 3 hours followed by 90° C for 3 hours.

(B) Asbestos fibers of the type used in Example 1 (B), 3.7 parts, and 370 parts of distilled water were placed in a blender. To this was then added a mixture of

| | | |
|---|---|---|
| dispersion of (A) | 6.95 | parts |
| methanol | 40 | parts |
| dispersion of a TFE/HFP 85/15 copolymer in water (55% solids) | 1.11 | parts |
| distilled water | 20 | parts |

The charge was blended at low speed for 10 minutes and the resulting slurry was then diluted with 1558 parts of distilled water. The liquid was drawn from this slurry in a Buechner funnel under a vacuum of 250 mm.

The resulting mat was dried under light pressure at 25° C for 5 minutes, then at 95° C for 30 minutes, and finally baked at 275° C for 30 minutes, to give a product 2.5 mm thick.

The mat was then boiled for 90 minutes in 5% aqueous sodium hydroxide.

(C) The mat prepared in (B) was put in the diaphragm position on the cathode of a chlor-alkali cell, where, in operation, it required an average voltage of 3.26 to achieve a current density of 0.204 amperes per square centimeter of diaphragm area.

Example 2 can be repeated except that the tetrafluoroethylene used in (A) is replaced with an equal amount of a 50/16 mixture of tetrafluoroethylene and bromotrifluoroethylene. Results will be substantially the same.

EXAMPLE THREE (A) A fluorotelomer was prepared as described in Example 1 (A) using the following charge
(1) a solution of 12 parts of tetraethyl pyrophosphite in 120 parts of trichlorotrifluoroethane
(2) a solution of 3.65 parts of di-t. butyl peroxide in 40 parts of trichlorotrifluoroethane
(3) a mixture of 50 parts of tetrafluoroethylene and 10 parts of perfluoropropyl vinyl ether and holding the reaction temperature at 100° C for 2 hours, at 120° C for another 2 hours, and then at 140° C for 2 hours.

(B) A slurry of

| Distilled water | 2420 | parts |
| Sodium chloride | 263 | parts |
| Asbestos (same type as in Example 1) | 24.2 | parts | was sparged with air for 2 hours. To the slurry was added a dispersion of

| (1) | Dispersion of the telomer of (A), 3.03 parts in 14.91 parts of methanol | | |
| (2) | TFE/HFP 85/15 copolymer powder | 3.03 | parts |

The slurry was sparged with air for 30 minutes and then blended in a blender for 1 minute at medium speed.

A mat was prepared from the slurry by drawing off the liquid in a sheet mold under a vacuum of 250 mm of mercury. The mat was washed by drawing 2000 parts of distilled water through it, was pressed between sheets of absorbent paper and then held at 135° C for 5 minutes, still between the sheets of paper.

The resulting dry mat, 1.5 mm thick, was then baked for 30 minutes at 275° C.

(C) The mat prepared in (B) was put in the diaphragm position on the cathode of a chlor-alkali cell, where, in operation, it required an average voltage of 2.96 to achieve a current density of 0.129 amperes per square centimeter.

Example three can be repeated except that the fluoromonomer charge in (A) is replaced with an equimolar amount of a 80/20 mixture of tetrafluoroethylene and hexafluoropropylene. Results will be substantially the same.

EXAMPLE FOUR (A) A fluorotelomer was prepared as described in Example 1 (A) using the following charge
(1) a solution of 12 parts of tetraethyl pyrophosphite in 120 parts of trichlorotrifluoroethane
(2) a solution of 3.65 parts of t. butyl perpivalate in 40 parts of trichlorotrifluoroethane
(3) a mixture of 50 parts of TFE and 15 parts of HFP and holding the reaction temperature at 60° C for 2 hours and then at 80° C for 2 hours.

(B) A slurry of

| Distilled Water | 2420 | parts |
| Sodium chloride | 263 | parts |
| Asbestos (same type as in Example 1) | 24.2 | parts | was sparged with air for two hours. To the slurry was added a dispersion of

| (1) | a dispersion of the telomer of (A), 4.54 parts in 50 parts of methanol | | |
| (2) | TFE/HFP 18/15 copolymer powder | 1.90 | parts |

The slurry was sparged with air for two hours and then blended for one minute in a blender at medium speed.

A mat was prepared from the slurry as in Example 3(B).

(C) The mat prepared in (B) was put in the diaphragm position on the cathode of a chlor-alkali cell, where, in operation, the average voltages indicated below were required to achieve the current densities indicated.

| Volts | Amperes/cm$^2$ |
| --- | --- |
| 2.86 | 0.129 |
| 3.04 | 0.182 |
| 3.10 | 0.204 |

Such results are also obtained when the diaphragm is formed by similar techniques directly on the cathode.

What I claim is:

1. A fluorotelomer represented by the structure

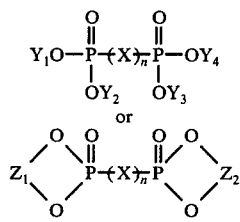

where $Y_1$, $Y_2$, $Y_3$ and $Y_4$ are the same or different and are alkyl radicals of 1–10 carbon atoms or alkyl radicals of 1–10 carbon atoms substituted with at least one alkyl radical of 1–4 carbon atoms;

X is a homo- or cotelomeric moiety of at least one of
(a) one or more monoethylenically unsaturated monomers fully substituted with fluorine atoms or with a combination of at least one fluorine atom and chlorine or bromine atoms, and
(b) a perfluoroalkyl vinyl ether whose alkyl group contains 1–10 carbom atoms;

$Z_1$ and $Z_2$ are the same or different and are alkylene radicals of 1–10 carbon atoms, or alkylene radicals of 1–10 carbom atoms substituted with at least one alkyl radical of 1–4 carbon atoms, or $Z_2$ is made up of $Y_1$ and $Y_2$; and $n$ is 2–500.

2. The fluorotelomer of claim 1 wherein $Y_1$, $Y_2$, $Y_3$ and $Y_4$ are ethyl.

3. The fluorotelomer of claim 1 wherein $Y_1$, $Y_2$, $Y_3$ and $Y_4$ are butyl.

4. The fluorotelomer of claim 1 wherein $Y_1$ and $Y_2$ are ethyl and $Y_3$ and $Y_4$ are butyl.

5. The fluorotelomer of claim 1 wherein $Y_1$ and $Y_2$ are ethyl, $Y_3$ and $Y_4$ are butyl, X is a telomeric moiety of TFE and $n$ is 20–100.

6. The fluorotelomer of claim 1 wherein X is a cotelomeric moiety of tetrafluoroethylene and perfluoropropyl vinyl ether; $Y_1$, $Y_2$, $Y_3$ and $Y_4$ are ethyl; and $n$ is 20–100.

7. A composition suitable for preparing a diaphragm for an electrolytic cell containing a cell liquor, comprising
   (a) 10–90%, by weight of the total of (a) and (b), of at least one telomer according to claim 1;
   (b) 10–90%, by weigt of the total of (a) and (b), of a fluoropolymer binder;
   (a) plus (b) constituting 10–90% by weight of the total of (a), (b) and (c),
   (c) 10–90%, by weight of the total of (a), (b) and (c) of a fibrous material resistant to attack by the cell liquor; and
   (d) a liquid carrier.

8. The composition of claim 7 where, in the fluorotelomer of (a), $Y_1$, $Y_2$, $Y_3$ and $Y_4$ are ethyl.

9. The composition of claim 7 where, in the fluorotelomer of (a), $Y_1$, $Y_2$, $Y_3$ and $Y_4$ are butyl.

10. The composition of claim 7 where, in the fluorotelomer of (a), $Y_1$ and $Y_2$ are ethyl and $Y_3$ and $Y_4$ are butyl.

11. The composition of claim 7 where, in the fluorotelomer of (a), X is a telomeric moiety of TFE, $Y_1$ and $Y_2$ are ethyl, $Y_3$ and $Y_4$ are butyl and $n$ is 20–100; the binder in (b) is a tetrafluoroethylene/hexafluoropropylene copolymer; the fibers in (c) are of asbestos and the carrier in (d) is brine.

12. The composition of claim 7 where, in the fluorotelomer of (a), X is a cotelomeric moiety of tetrafluoroethylene and perfluoropropyl vinyl ether.

13. The composition of claim 7 where, in the fluorotelomer of (a), X is a cotelomeric moiety of tetrafluoroethylene and perfluoropropyl vinyl ether, $Y_1$, $Y_2$, $Y_3$ and $Y_4$ are ethyl and $n$ is 20–100; the binder in (b) is a tetrafluoroethylene/hexafluoropropylene copolymer; the fibers in (c) are of asbestos and the carrier in (d) is brine.

14. A composition consisting essentially of
   (a) 1–99%, by weight of the total of (a) and
   (b), of a fluorotelomer according to claim 1; and
   (b) 1–99%, by weight of the total of (a) and (b), of a fluoropolymer.

15. A process for preparing the fluorotelomer of claim 1, comprising bringing at least one of
   (a) one or more monoethylenically unsaturated monomers fully substituted with fluorine atoms or with a combination of at least one fluorine atom and chlorine or bromine atoms, and
   (b) a perfluoroalkyl vinyl ether whose alkyl group contains 1–10 carbon atoms,
into contact with a compound capable of generating a free radical of the structure

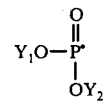

where $Y_1$ and $Y_2$ are the same or different and are alkyl radicals of 1–10 carbon atoms or alkyl radicals of 1–10 carbon atoms substituted with at least one alkyl radical of 1–4 carbon atoms,
under conditions suitable for reaction.

16. A process according to claim 15 wherein the fluorotelomer is subsequently hydrolyzed to conveert $Y_1$ and $Y_2$ to hydrogens by contact with acids.

17. A process according to claim 15 wherein the fluorotelomer is subsequently converted to the salt form wherein $Y_1$ and $Y_2$ are metals by contact with a salt of the selected metals.

18. A process according to claim 15 wherein the compound capable of generating the free radical is a tetraalkyl pyrophosphite.

19. A process according to claim 15 wherein the compound capable of generating the free radical is a tetraalkyl hypophosphate.

20. A process according to claim 15 wherein the compound capable of generating the free radical is a cycloalkyl hypophosphate.

21. A process according to claim 15 wherein the compound capable of generating the free radical is a cycloalkyl pyrophosphite.

22. A process according to claim 15 wherein the compound capable of generating the free radical has the structure

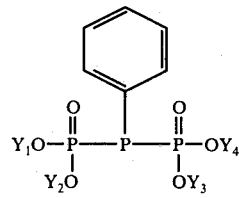

wherein $Y_1$, $Y_2$, $Y_3$ and $Y_4$ are the same or different and are alkyl radicals of 1–10 carbon atoms or alkyl radicals of 1–10 carbon atoms substituted with at least one alkyl radical of 1–4 carbon atoms.

* * * * *